(12) United States Patent
Scheffler et al.

(10) Patent No.: US 7,805,974 B2
(45) Date of Patent: *Oct. 5, 2010

(54) TESTING PERFORMANCE OF GAS MONITORS

(75) Inventors: Arthur Scheffler, Surrey (CA); Cristian D. Nanea, Vancouver (CA)

(73) Assignee: 3M Innovative Properties Company, St. Paul, MN (US)

(*) Notice: Subject to any disclaimer, the term of this patent is extended or adjusted under 35 U.S.C. 154(b) by 191 days.

This patent is subject to a terminal disclaimer.

(21) Appl. No.: 12/055,828

(22) Filed: Mar. 26, 2008

(65) Prior Publication Data

US 2008/0173066 A1   Jul. 24, 2008

Related U.S. Application Data

(63) Continuation of application No. 11/551,828, filed on Oct. 23, 2006, now Pat. No. 7,377,147.

(51) Int. Cl.
*G11N 1/21* (2006.01)

(52) U.S. Cl. ..................................... 73/1.06

(58) Field of Classification Search ............... None
See application file for complete search history.

(56) References Cited

U.S. PATENT DOCUMENTS

| | | | |
|---|---|---|---|
| 3,851,520 A | 12/1974 | Schluter et al. |
| 4,411,156 A | 10/1983 | Lowe |
| D282,449 S | 2/1986 | Richardson |
| 5,179,924 A | 1/1993 | Manaka |
| 5,409,583 A | 4/1995 | Yoshioka et al. |
| 5,573,953 A | 11/1996 | Marnie et al. |
| 5,714,046 A | 2/1998 | Lauer et al. |
| 5,764,150 A | 6/1998 | Fleury et al. |
| 5,777,207 A | 7/1998 | Yun et al. |
| 6,107,925 A | 8/2000 | Wong |
| 6,144,310 A | 11/2000 | Morris |
| 6,172,759 B1 | 1/2001 | Goldstein |
| 6,234,006 B1 | 5/2001 | Sunshine et al. |
| 6,244,093 B1 | 6/2001 | Parekh |
| 6,282,940 B1 | 9/2001 | Hung et al. |
| 6,426,703 B1 | 7/2002 | Johnston et al. |
| 6,437,692 B1 | 8/2002 | Petite et al. |
| 6,479,833 B1 | 11/2002 | Pfefferseder et al. |
| 6,588,250 B2 | 7/2003 | Schell |

(Continued)

FOREIGN PATENT DOCUMENTS

JP    2115741    4/1990

(Continued)

OTHER PUBLICATIONS

U.S. Appl. No. 11/551,843, filed Oct. 23, 2006 to Scheffler entitled *Gas Monitor Testing Apparatus, Method, and System.*

(Continued)

*Primary Examiner*—Robert R Raevis
(74) *Attorney, Agent, or Firm*—Anna A. Wetzels

(57) ABSTRACT

Method, apparatus, and system are utilized for testing the performance of a gas monitor against predetermined monitor characteristics to determine if performance of the gas monitor is validated in a manner whereby testing gas is directly delivered to the gas sensor.

19 Claims, 8 Drawing Sheets

U.S. PATENT DOCUMENTS

| | | |
|---|---|---|
| 6,753,786 B1 | 6/2004 | Apperson et al. |
| 6,769,285 B2 * | 8/2004 | Schneider et al. ............ 73/1.06 |
| 6,791,453 B1 | 9/2004 | Andres et al. |
| 6,819,252 B2 | 11/2004 | Johnston et al. |
| 6,840,086 B2 | 1/2005 | McCoy et al. |
| 6,883,364 B2 | 4/2005 | Sunshine et al. |
| 6,920,461 B2 | 7/2005 | Hejlsberg et al. |
| 6,948,352 B2 | 9/2005 | Rabbett et al. |
| 6,957,562 B2 | 10/2005 | Anilovich et al. |
| 7,082,810 B2 | 8/2006 | Sakamoto et al. |
| 2001/0018844 A1 | 9/2001 | Parekh |
| 2002/0044061 A1 * | 4/2002 | Johnston et al. ............ 340/628 |
| 2002/0157447 A1 | 10/2002 | Schell |
| 2003/0150252 A1 | 8/2003 | Wang et al. |
| 2004/0135695 A1 | 7/2004 | Barton et al. |
| 2005/0016253 A1 * | 1/2005 | Anilovich et al. ............ 73/1.06 |
| 2005/0240943 A1 | 10/2005 | Smith et al. |
| 2006/0114115 A1 | 6/2006 | Smith et al. |

FOREIGN PATENT DOCUMENTS

| | | |
|---|---|---|
| KR | 20-0367856 | 11/2004 |
| KR | 10-2006-0068574 | 6/2006 |
| KR | 10-2006-0078312 | 7/2006 |
| KR | 10-2007-008796 A | 8/2007 |
| WO | WO 02/48705 A2 | 6/2002 |
| WO | WO 2006/132745 A1 | 12/2006 |

OTHER PUBLICATIONS

U.S. Design Patent Application Serial No. 29/249,818, filed Oct. 23, 2005 to Scheffler entitled *Test Gas Delivery Device*.

*UL 2034 Short History-CO Alarms*, International Code Council (Falls Church, VA), May 4, 2005, place of publication: www.iccsafe.org/cs/cc/ctc/CO/CO_UL2034History.pdf.

Testing Instructions for CM-15/15A Carbon Monoxide Detectors, Macurco (Jul. 2006).

Macurco Carbon Monoxide Field Test and Certificate Kit For Testing and Certifying CM-15 and CM-15A Carbon Monoxide Detectors(Jul. 2006).

Picture of parts for CM-15 Field Test Kit.

Picture of front view of parts for CM-15 Field Test Kit.

Picture of back view of parts for CM-15 Field Test Kit.

* cited by examiner

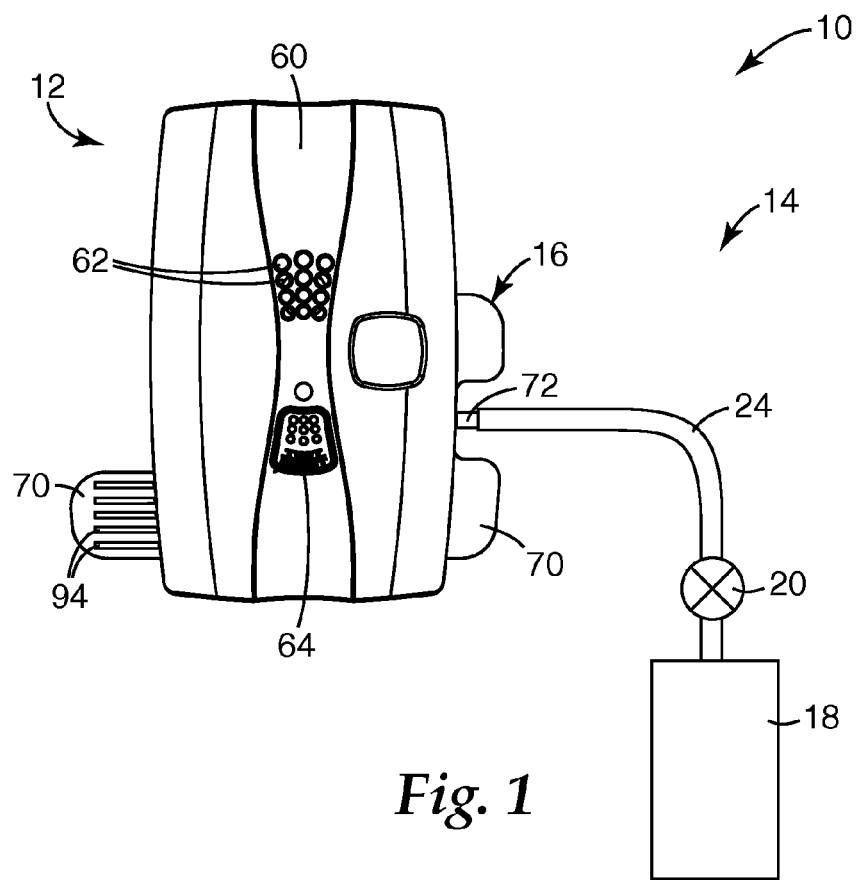
Fig. 1
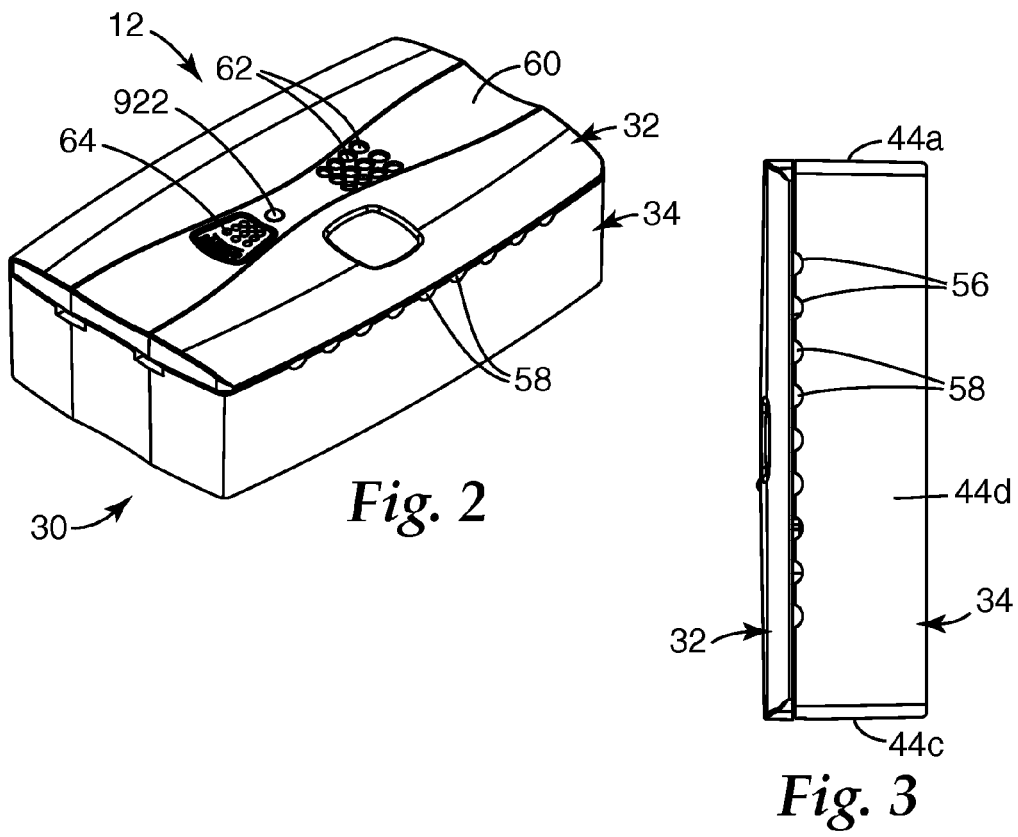
Fig. 2
Fig. 3

TESTING PERFORMANCE OF GAS MONITORS

CROSS REFERENCE TO RELATED APPLICATION

This application is a continuation of U.S. Ser. No. 11/551,828, filed Oct. 23, 2006 now U.S. Pat. No. 7,377,147, the disclosure of which is incorporated by reference in its entirety herein.

The present invention relates to gas testing processes, apparatus, and systems and, more particularly, to testing processes, apparatus, and systems for validating performance of gas monitors, such as carbon monoxide monitors.

A variety of toxic gases are monitored for dangerous concentrations. One such gas is carbon monoxide, (CO), a colorless, tasteless, odorless, and deadly gas. CO in high concentrations is not only undetectable by humans but is also highly dangerous and widely prevalent in many everyday situations. For instance, carbon monoxide can be produced by combustion of a number of common household sources, including wood or gas fireplaces, gas or oil furnaces, wood stoves, gas appliances, etc. CO typically becomes unsafe when dangerous concentrations build-up due to, for example, poor ventilation. CO build-up is a potential problem, for example, in energy-efficient, airtight homes, vehicles, and plants that decrease the exchange of inside and outside air.

CO monitors are commonly used to determine if the level of CO gas in the air has become dangerous. These devices continuously monitor the air for impermissible CO concentrations. The monitors calculate whether CO levels are high enough to pose a risk of dangerous buildups in the human body. If CO levels become so high, the monitors will issue an alarm.

To ensure adequate environmental monitoring, CO monitors are routinely checked to confirm their reliability. Prior attempts to provide performance validation typically occur after a monitor is manufactured and again after the monitor has been installed. Known validation protocols require the monitors to be tested over generally prolonged testing periods.

Known testing procedures generally require lengthy testing times because the sensor must reach an equilibrium response to the test gas before testing can proceed. Some testing procedures may take 10-15 minutes, while others may take up to 4 hours, depending on the nature of the monitor's specifications. For example, a gas sensor may be validated if a reading of the sensor (a) occurs within a time (usually several minutes or longer) based on the sensor reaching greater than 90% of its equilibrium response; and, (b) falls within an acceptable range of values based on the concentration of testing gas being used. Since testing procedures use testing gas, and given the relatively lengthy times required for a validating a monitor's performance, considerable testing gas may be used. It will be appreciated that there are cost considerations when frequently using relatively expensive testing gases for the significant periods of time as noted above, especially when such costs are multiplied by the number of sensors to be monitored and the number of times the monitors will be tested. If the testing gas is toxic, undesirable safety issues may also be present, should the gas not be handled properly or the testing procedure not be properly carried out.

As noted, many known testing procedures apply a testing gas to the detector. Known procedures may simulate conditions in which an alarm signal would issue a warning when exposed to undesirable levels of such a gas. Typically, such testing is performed by applying the test gas from a gas canister to a region or space exterior of the gas monitor's housing. Generally, considerable care is exercised in order to insure proper delivery of the testing gas in a safe manner. In one specific example, a gas impervious plastic bag surrounds the gas monitor for confining the gas during testing. A gas delivery tube has one end connected to a gas regulator associated with a testing gas canister and a gas delivery end connected to the plastic bag. The gas delivery tube end and plastic bag are placed exterior of and in close proximity to the gas monitor during the testing. The same user also opens the regulator and applies the testing gas. The user must wait for a specified time for insuring that the test protocol is followed. Typically, for such a gas monitor to pass a test, an alarm should sound within period of about 10-15 minutes. This is a considerable amount of time to expend not only in terms of holding the delivery tube and plastic bag in proper position over the gas monitor, but also for using the relatively expensive testing gas. This approach also tends to increase the time to validate a gas monitor because the applied testing gas must purge the volume of air surrounding the gas sensor, whereby the sensor can react to a constant level of testing gas at the desired level of testing gas concentration. Accordingly, not only is the amount of actual testing time at the desired level of testing gas concentration relatively lengthy, but the actual time to set-up and perform a test is increased due to additional time delays arising from setting up the test and purging the air.

SUMMARY OF THE INVENTION

The present invention provides an enhanced method, apparatus, and system utilized for testing the performance of a gas monitor against predetermined monitor characteristics to determine if performance of the gas monitor is validated in a manner that improves over prior art approaches.

The foregoing shortcomings are overcome or minimized by a method, apparatus and system of testing performance of a gas monitor, comprising: applying a testing gas adjacent a gas monitor; obtaining a first reading value of testing gas; storing the first reading value; obtaining a second gas monitor reading value; determining a rate-of-rise value of the first and second reading values based on a difference of the first and second reading values relative to a testing time interval therebetween; and, determining if a gas monitor passing condition exists based on a comparison of the rate-of-rise value to at least a predefined rate-of-rise value of the gas monitor.

The present invention also includes a gas monitor apparatus comprising: an enclosure; and, an electronic control assembly within the enclosure; the electronic control assembly including a gas sensor assembly for providing readings of testing gas proximate thereto; the electronic control assembly including at least a processor, a memory coupled to at least one processor, and a program which includes a testing module residing in the memory and executable by the processor, wherein the testing module in response to being invoked is operable for significantly reducing time for testing the gas sensor assembly relative to the gas sensor assembly operating at least in a normal mode of operation.

The present invention also includes a gas monitor system, the gas monitor system comprising: a gas monitor apparatus; a fluid coupling apparatus for fluidly coupling a source of testing gas to the gas monitor apparatus; the gas monitor apparatus includes an enclosure; and, an electronic control assembly within the enclosure; the electronic control assembly including a gas sensor assembly for providing readings of gas proximate thereto; the electronic control assembly including at least a processor, a memory coupled to the at least one processor, and a program which includes a testing module residing in the memory and executable by the processor, wherein the testing module in response to being invoked is operable for significantly reducing time for testing the gas sensor assembly relative to the gas sensor assembly operating at least in a normal mode of operation.

The present invention also includes an apparatus for testing gas response of a gas sensor assembly, wherein the apparatus comprises: at least a processor, a memory coupled to the at least one processor, and a program which includes a testing module residing in the memory and executable by the processor, wherein the testing module is operable in response to being invoked for significantly reducing the time for testing the gas sensor relative to the gas sensor assembly operating at least in a normal mode of operation.

An aspect of the invention is a method, apparatus, and system to compare the rate-of-rise value to at least a second predefined rate of rise value of the gas monitor to additionally predict if the gas monitor apparatus performs in the intended manner.

An aspect of the invention is a method, apparatus, and system to provide an extremely quick and inexpensive validation of the performance of gas monitors.

Another aspect of the invention is a method, apparatus, and system that achieve the foregoing in a manner that confirms performance of the gas monitor while using significantly less testing gas than prior approaches, thereby being highly economical.

Still another aspect of the invention is a method, apparatus, and system that achieve the foregoing in a manner that minimizes significantly the time of testing CO monitors.

Another aspect of the invention is a method, apparatus, and system that determine if the gas monitor apparatus will perform in its intended manner without having to run the monitor through a complete testing cycle.

Another aspect of the invention is the utilization of first and second predetermined rate-of-rise values for defining bounds of acceptable validating performances of the gas sensor assembly being tested.

The aspects described herein are merely a few of the several that can be achieved by using the present invention. The foregoing descriptions thereof do not suggest that the invention must only be utilized in a specific manner to attain the foregoing aspects.

These and other features and aspects of this invention will be more fully understood from the following detailed description of the preferred embodiments. It should be understood that the foregoing generalized description and the following detailed description are exemplary and are not restrictive of the invention

GLOSSARY

The term "equilibrium response" as used in the specification and claims defines a response when the sensor output of the gas sensor of the gas monitor apparatus being tested no longer increases.

BRIEF DESCRIPTION OF THE DR WINGS

FIG. 1 is a schematic view of a system of this invention that includes a field test kit in combination with the gas system of this invention.

FIG. 2 is a perspective view of a gas monitor apparatus made according to the present invention.

FIG. 3 is a side view of the gas monitor apparatus illustrated in FIG. 2.

DETAILED DESCRIPTION OF PREFERRED EMBODIMENTS

Figure 4:
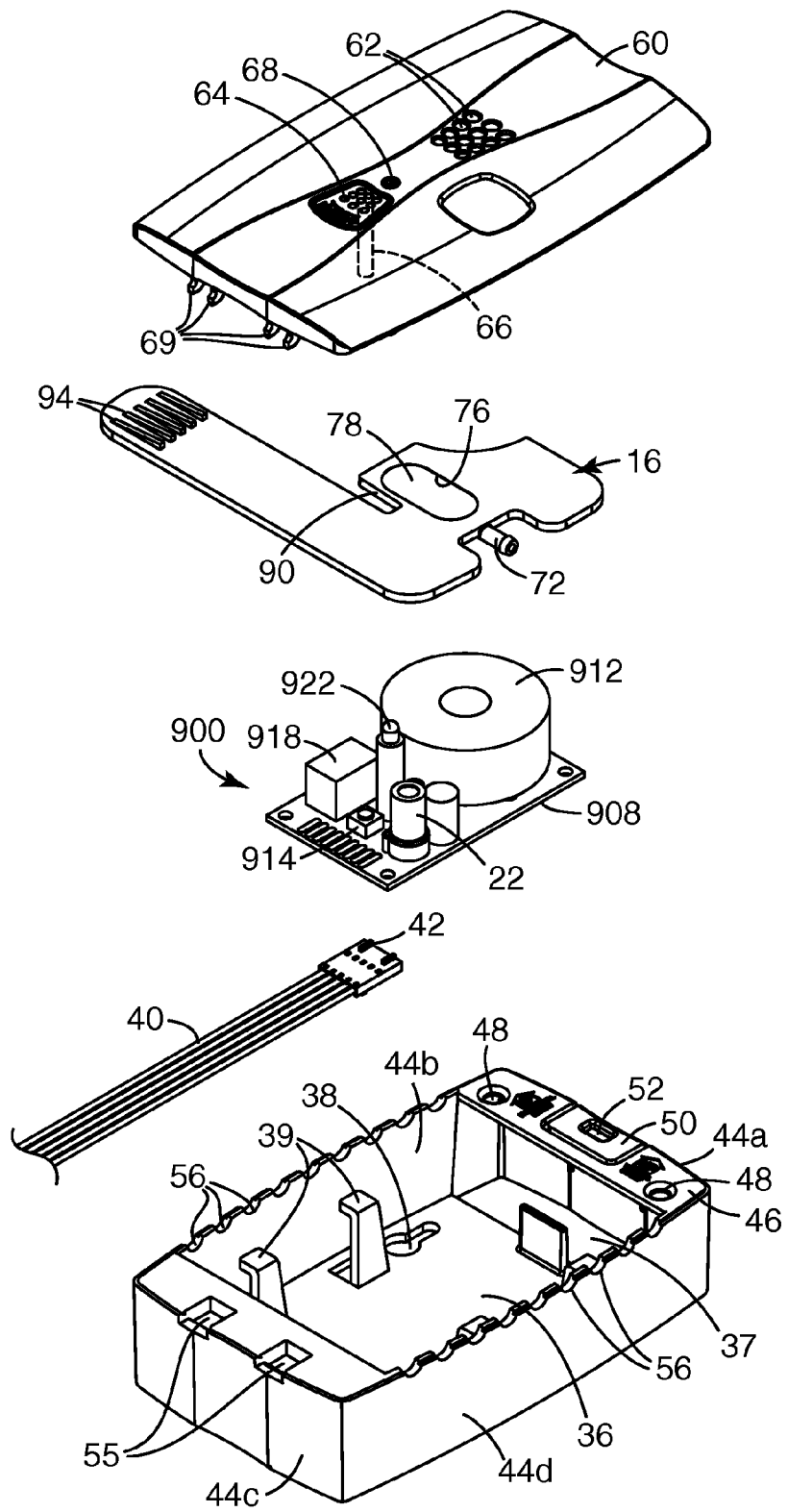
FIG. 4 is an exploded perspective view of the gas monitor apparatus illustrated in FIGS. 2 and 3.

The words "a", "an", and "the" are used interchangeably with "at least one" to mean one or more of the elements being described. By using words of orientation, such as "top", "bottom", "overlying", "front", "back" and "backing" and the like for the location of various elements in the disclosed articles, we refer to the relative position of an element with respect to a horizontally-disposed body portion. We do not intend that the disclosed articles should have any particular orientation in space during or after their manufacture.

FIG. 1 is a schematic view of a gas monitoring system 10 of this invention operable for confirming performance of a carbon monoxide gas monitor apparatus 12. Included in the gas monitoring system 10 is a field test kit assembly 14. The field test kit assembly 14 includes a fluid coupling apparatus 16 also made according to this invention. The fluid coupling apparatus 16 is adapted to couple a source of testing gas, such as from a testing gas canister 18 that flows through a regulator 20, to a gas sensor assembly 22 (FIG. 4) within in the gas monitor apparatus 12 by way of flexible tubing 24. While the illustrated embodiment is described in the context of a carbon monoxide gas monitor apparatus 12, this invention is broadly capable of validating performances of not only other kinds of CO gas monitors, but other gas monitors for other gases as well. This testing determines whether the gas monitor apparatus satisfies its performance criteria without the gas monitor apparatus having to run a complete test. Basically, the testing is accomplished in durations much shorter than the normal testing periods for CO gas monitors. Accordingly, the shorter testing periods produce, significant savings since less testing gas is consumed than otherwise and the attendant testing labor costs are reduced.

The gas monitor apparatus 12 is adapted for operation in home or commercial environments although it may be operated in a variety of other environments. As illustrated in FIGS. 1-4, the gas monitor apparatus 12 may have a generally parallelepiped enclosure or housing assembly 30. The housing assembly 30 may be made of any suitable materials such as a thermoplastic material as polycarbonate, ABS or the like. The housing assembly 30 can have a variety of configurations and includes essentially a front cover assembly 32 removably attached to a back plate assembly 34. The back plate assembly 34 includes an intermediate flat back wall 36 which defines openings 37 at opposite ends thereof (only one of which is shown in FIG. 4). The back wall 36 has suitable apertures 38 (one of which is shown) that facilitate attachment to any suitable supporting structure (not shown). The back wall 36 may have other configurations and be structured differently for enabling the attaching thereof to other kinds of supporting structures. For example, the back wall 36 may have suitable structure (not shown) for allowing releasable attachment to an electric box (not shown), such as when the gas monitor apparatus 12 is to be hardwired. Also, the back wall 36 may have other structure, such as projections 39 for allowing routing of a wiring harness 40 (FIG. 4) attached to a connector 42. The connector 42 is attached to the electronic control assembly. The openings 37 allow the wiring to extend out of the gas monitor 12 for coupling to a power source. Other suitable housing construction for battery powered or main powered are envisioned.

The sidewalls 44a-44d extend upwardly relative to the back wall 36 as viewed in FIG. 4. The top sidewall 44a includes an overhang portion 46 that includes a pair of spaced apart openings 48. A user depressible finger latch 50 is integrally formed into the sidewall 44a. The finger latch 50 has a latch opening 52 in a distal portion that lies within the overhang thereof for releasable cooperation with a tab 54 (FIG. 7) extending laterally from an inner wall of the front cover assembly 32. The finger latch 50 is normally biased to latch with the tab 54 to retain the former to the latter. A pair of spaced apart openings 55 is in the bottom sidewall 44c for cooperating with the front cover assembly 32.

As illustrated in FIG. 4, the sidewalls 44b and 44d have a series of scalloped portions 56 along their edges, such that when they mate with a surface of the front cover assembly 32 they define a series of lateral openings 58 (FIGS. 2 & 3). The lateral openings 58 allow for ambient air to travel into and through the interior of the gas monitor apparatus 12 for sensing purposes. A pair of spaced apart projections 59 (FIG. 7) is adapted to cooperate with the openings 48 on the back plate assembly so as to assist in properly mating the latter to the front cover assembly, whereby the front cover assembly can pivot relative to the back plate assembly between open and closed conditions. While the present embodiment discloses the foregoing such structure for effecting pivoting, other approaches for pivotally or otherwise opening the front cover assembly 32 of the gas monitor apparatus 12 are envisioned.

The front cover assembly 32 has a generally rectangular shape panel portion 60 formed with a series of openings 62 that facilitate passage of air and sound therethrough. The front cover assembly 32 also includes a finger actuated switch element 64 depressed by a user from its normally non-operative state to an operative state or testing mode for actuating a gas testing process in accordance with this embodiment. In this embodiment, the finger actuated switch element 64 includes an actuator rod 66 (FIG. 4) that is connected to an underneath portion of the switch element 64 and is adapted to engage a switch as will be described. In addition, a display opening 68 is provided, whereby a display, to be described, can protrude for display purposes. In addition, a pair of spaced apart curved legs 69 (FIG. 4) is normally adapted to be positioned within the openings 55 and cooperates with the back plate assembly for allowing the front cover and back plate assemblies 32, 34; respectively, to be generally pivotally moved, as in a clam-shell fashion, between a closed condition (FIG. 2) and an open position (not shown) as is known. The present invention contemplates a variety of other suitable approaches for releasably joining the two assemblies together.

Fluid Coupling Apparatus of Field Test Kit

In FIGS. 4-7 the fluid coupling apparatus 16 is seen as being constructed to allow delivery of testing gas to the gas monitor apparatus 12 in an easy and inexpensive fashion. As such, this allows field testing to be more easily accomplished. In particular, the fluid coupling apparatus 16 is removably couplable to the gas monitor and delivers the testing gas to a region positioned immediately adjacent a gas sensor assembly, thereby making for a more efficient testing process as will be explained. The regulator 20 (FIG. 1) is controlled by the user for controlling the testing gas admitted into the tubing 24 and that flows to the gas monitor apparatus 12.

The fluid coupling apparatus 16 may be defined by an elongated and thin fluid coupler body 70 that may be made of a suitable thermoplastic material, such as nylon, polycarbonate, ABS or the like. Other suitable materials and constructions of the housing assembly are contemplated. The tubing is releasably coupled to a tube barb 72 protruding generally longitudinally therefrom so as to be exteriorly located when the fluid coupling apparatus is in the testing mode. An internal passageway 74 (FIGS. 5A, 5B, 5C & 7) is formed in the fluid coupler body 70 and extends through the tube barb 72 and terminates in a laterally disposed recess 76 (FIG. 5B) formed intermediate the length of the fluid coupler body 70. While a fluid passageway is formed internally, the present invention envisions that the fluid passageway may be external to the fluid coupler body 70.

The fluid coupler body 70 is also provided with a gas sealing member 78 that serves to cover one portion of the recess 76 to provide a gas seal. The gas sealing member 78 may be a thin plastic or the like that covers the recess 76 in a flush manner to provide the gas seal. The recess 76 has an enlarged mouth portion into which the testing gas enters as it exits the passageway 74

Figure 5A:
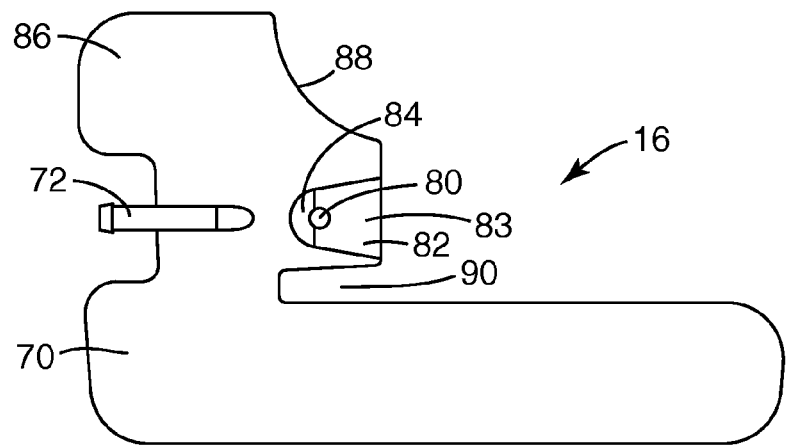
FIG. 5A is a front view of a fluid coupler apparatus made according to the present invention.
Figure 5B:
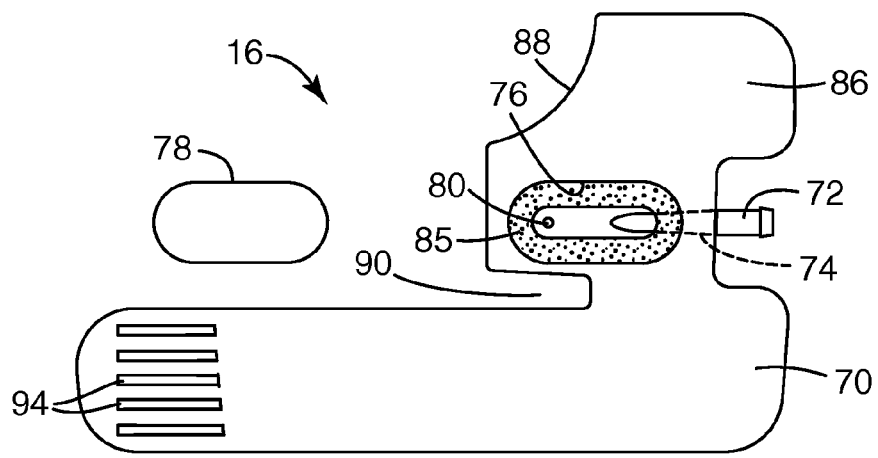
FIG. 5B is a rear view of a fluid coupler apparatus made according to the present invention.
Figure 5C:
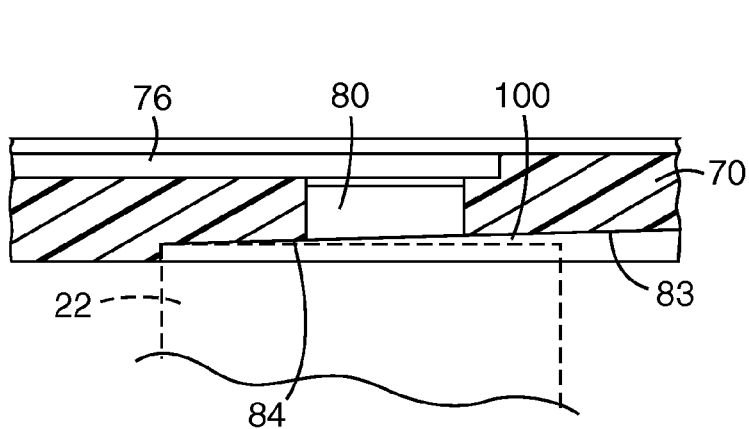
FIG. 5C is an enlarged cross-sectional view of a part of the fluid coupler apparatus illustrating a gas opening delivery opening in a locating recess.
Figure 6:
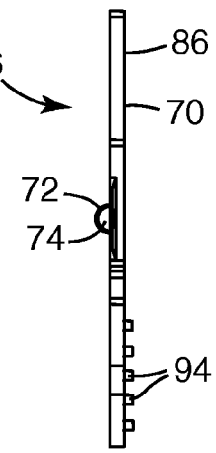
FIG. 6 is a right side view of the fluid coupler apparatus illustrated in FIG. 5.

Reference is made to FIG. 5B for illustrating a gas delivery opening 80 in fluid communication with the recess 76. On the other side of the fluid coupler body 70, as shown in FIGS. 5A and 5C, the gas delivery opening 80 is adjacent a locating recess 82. The locating recess 82 provides a tapered area for facilitating delivery of the testing gas to the gas sensor assembly 22. A purpose of the wider to narrower taper (FIG. 5A) of the locating recess 82 is to capture a top portion of the gas sensor in the fluid coupler body 70 as the latter is slid over the gas sensor. A tapered ramp portion 83 extends from the edge of the fluid coupler body and ends in a small generally flat semi-circular sensor engaging portion or area 84. A purpose of the ramp portion 83 is to allow the gas sensor to engage and capture the fluid coupler body 70 on the ramp rather than jamming against the edge of the fluid coupler body. When fully engaged or coupled, the gas sensor has traveled all the way up the ramp portion 83 and is firmly seated (FIG. 5C) against the sensor engaging portion 84 so that the gas sensor 22 is centered under the gas delivery opening 80. The resiliently deformable plastic fluid coupler body 70 is pressed away from the gas sensor, but owing to its resilient nature remains against the surface of the gas sensor due to the resilient nature of the fluid coupler body 70. Because of the slope of ramp portion 83 (FIG. 5C), a space or gap 100 exists above the gas sensor 22 to allow the testing gas to escape and activate the gas sensor. As a result, the gap 100 will remain generally repeatable for subsequent tests. This also ensures that the gas sensor is not sealed to the fluid coupler body 70 and that the test gas flows over the gas sensor to the edge of the fluid coupler body 70 for each test. In this manner, there is very little air to purge and the gas sensor can almost immediately react to a constant level of the testing gas. The gas delivery opening 80 and the tapered recess 82 are, in one embodiment, sized to be in overlying relationship and alignment with the gas sensor assembly. Other configurations and structures are envisioned for insuring the alignment and spacing of the gas delivery opening to a position proximate the gas sensor assembly as well for ensuring that the fluid coupler body does not jam against the gas sensor.

In the illustrated embodiment, the gas sealing member 78 is secured by an adhesive material 85 to the fluid coupler body 70. It will be appreciated that the recess 76 and gas opening 80 are arranged on the fluid coupler body 70 to be substantially aligned immediately adjacent or proximate the gas sensor assembly 22 (FIG. 7) when the fluid control body 70 is mated or otherwise coupled to the electronic control assembly and/or structure of the gas monitor apparatus. This advantageously insures testing gas being directly delivered to the gas sensor assembly instead of being applied to the exterior of the gas monitor. This promotes the purposes of efficient testing without wasting testing gas and reducing the amount of time for purging air.

The fluid coupler body 70 has an upstanding portion 86 provided with a curved stop segment or portion 88. The curved portion or stop segment 88 is sized and configured to engage a buzzer of the gas monitor apparatus 12 (see FIG. 7) and acts as a stop surface for inhibiting rotational and lateral displacement of the fluid coupler body 70. In addition, a slot 90 extends along a portion of the fluid coupler body 70 that permits the fluid coupler body 70 to slide into engagement with a stop segment that engages one of the mounting posts 92 (FIG. 7) of the front cover assembly 32. The end of the slot 90 provides a stop that limits displacement and provides alignment of the gas delivery opening relative to the gas sensor. As such, the fluid coupler body 70 is prevented or stopped from sliding laterally in one direction (downward, as viewed in FIG. 7). In the illustrated embodiment, the fluid coupler body 70 is provided with a series of spaced apart stop projections 94 on one end of a leg portion thereof. The stop projections 94 extend exteriorly from the mated front cover and back plate assemblies to thereby stop at least longitudinal sliding movement of the fluid coupler body 70 in an opposite direction (i.e., rightward, as viewed in FIG. 1). Other equivalent structure can be provided so as to limit or stop displacement of the fluid coupler body 70. As noted, this further prevents unwanted movement of the fluid coupler body 70 during the CO testing process. Hence, the tendency for unwanted sliding movement that may be caused by the weight of the gas canister 18 and the regulator 20 tugging or pulling on the fluid coupler body 70 during testing is minimized or avoided. Accordingly, there is a more secure testing environment insuring proper delivery of testing gas.

The fluid coupler body 70 is, as noted, to be mounted to the gas monitor apparatus 12 after the front cover assembly 32 is moved as by the legs 69 pivoting or otherwise moving relative to the openings 55 in the back plate assembly to an open position. Attachment of the fluid coupler body 70 is easily and quickly achieved because the fluid coupler body is constructed in a manner that provides a relatively high degree of certainty that the gas delivery opening 80 is properly aligned immediately adjacent the gas sensor assembly 22. Such relatively precise alignment optimizes the CO testing process thereby minimizing false readings. In addition, since the gas delivery opening is aligned and immediately adjacent the gas sensor assembly, the latter is exposed directly to the testing gas in a manner that reduces the need to purge air surrounding the gas sensor assembly. Accordingly, the gas sensor assembly experiences relatively quickly gas at a concentration level used for the testing, whereby testing at the desired gas concentration level may commence. Moreover, the present invention envisions that the fluid coupler body 70 may slide into an opening or slot (not shown) formed in a side of the gas monitor housing instead of having to open the front and back assemblies.

Electronic Control Assembly

Figure 7:
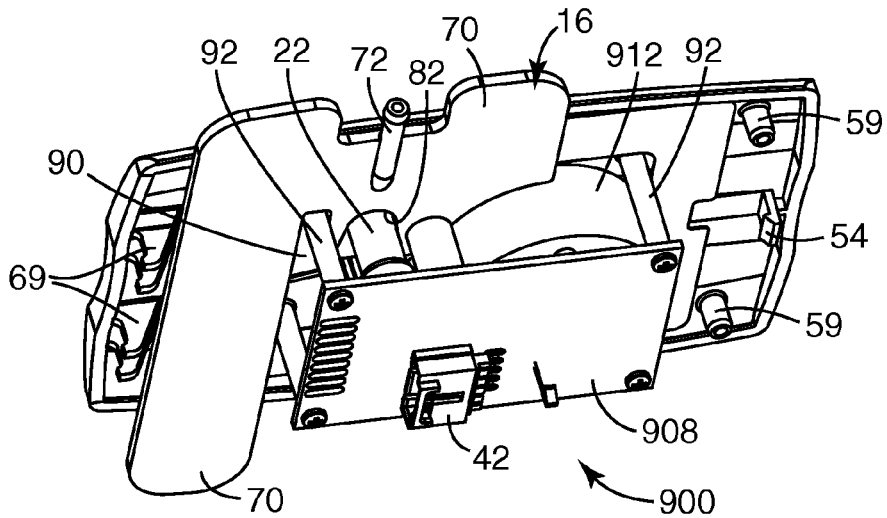
FIG. 7 is a view of the fluid coupler in a coupled condition relative to an electronic control assembly of this invention.
Figure 9:
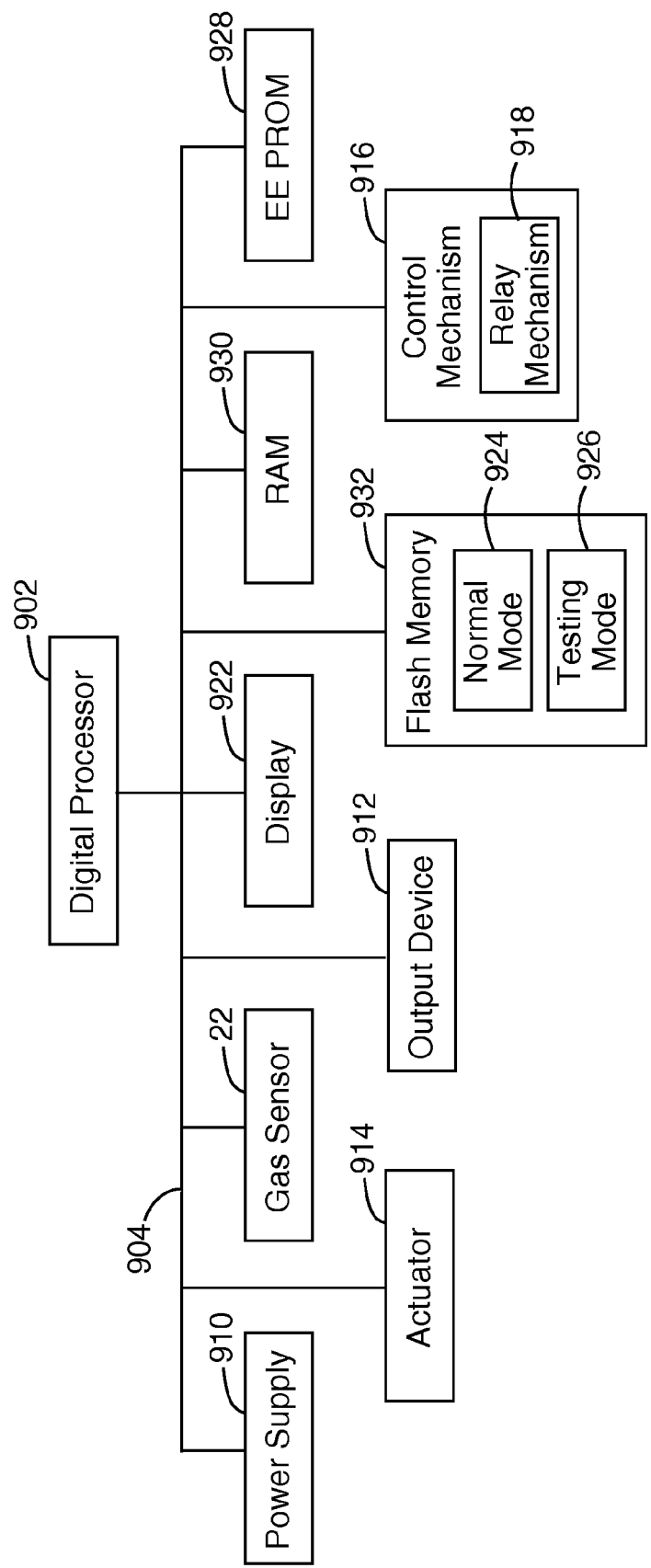
FIG. 9 is a simplified block diagram illustrating the electronic control assembly of this invention.

FIGS. 4, 7 and 9 illustrate aspects of an electronic control assembly 900. FIG. 9 is a simplified block diagram of an electronic control assembly 900 attached in spaced apart relationship to an interior surface of the front cover assembly 32. When the front cover assembly 32 is pivoted to its open condition, the fluid coupling apparatus 16 can then be easily and directly attached to the electronic control assembly 900 as illustrated in FIG. 7 to deliver the testing gas directly thereto.

In an exemplary embodiment, provision is made for a digital processor 902, such as, for example, a microcontroller, to be coupled to an information system bus 904. The information system bus 904 interconnects with the other components of the electronic control assembly 900. In an exemplary embodiment, the electronic control assembly 900 including the gas sensor assembly 22 may be mounted on a printed circuit board assembly 908. The gas sensor assembly 22 can be any suitable type. Typically, a semiconductor kind is utilized for monitoring CO gas in commercial units. More typically, the semiconductor gas sensor assembly 22 may be commercially available from Figaro U.S.A. Inc. of Glenview, Ill. Other suitable CO sensors are envisioned for use. As noted, the present invention is applicable for testing monitors for other gases as well. Hence, other types of gas sensors would be used.

The electronic control assembly 900 includes an output device 912, such as a buzzer unit 912 mounted on the printed circuit board assembly 908. The buzzer unit 912 operates to provide audible warning sounds to an operator/user in response to inappropriate levels of CO gas being detected by the gas sensor assembly 22. Other suitable output devices 912 that issue warnings in any desired manner are contemplated for use, for example, visual indicators (e.g., light-emitting diodes, etc.), third party alarm systems, display devices or the like.

An actuator switch 914 is mounted on the printed circuit board assembly 908. A distal end of the switch actuator rod 66 is spaced from a surface of the actuator switch 914. The actuator switch 914 is adapted to be contacted by the end of a switch actuator rod 66 and, as will be described, functions to initiate both the normal mode of operation and the CO testing mode process of this invention depending on the number of times the actuator switch 914 is actuated. Other suitable actuation schemes are contemplated. In the present invention a single switch is used for effecting normal and testing modes. However, other switching arrangements may be utilized to implement such modes of operation.

A control mechanism 916 includes a relay mechanism 918 which operate under the control of the digital processor 902. The relay mechanism 918 is used to send a signal to an external alarm device on a monitoring panel (not shown). Under the control of the digital processor 902 and in response to sensed conditions by the gas sensor assembly 22, in a normal operating mode, the digital processor 902 sends signals to activate, for example, the buzzer unit 912 that predetermined levels CO gas concentrations considered potentially harmful are present. The digital processor 902 may also provide other signals, such as when a replaceable battery (not shown) is running low. A power supply 910 is provided for providing power for the electronic control assembly 900. The power supply 910 may be hardwired and/or be a replaceable battery (not shown) to be housed in the gas monitor apparatus 12. The power supply 910 may be coupled to the wiring harness 40. The digital processor 902 (e.g., microcontroller) may act to control operation of a display 922 (e.g., light-emitting diode 922) in a known manner through display signals. In this embodiment, the display is a single element, but may be implemented in with any suitable display or number of displays. The signals of the light-emitting diode 922 may be manifested by different colors that flicker and/or are constant and their states are selected to be representative of certain desired operating conditions. Other similar and well-known implementations for providing displays that are indicative of different states of the gas monitor apparatus are envisioned. The light-emitting diode 922 is adapted to be in registry with the display opening 68 (FIG. 2).

The digital processor 902 may be any suitable type. The digital processor 902 is attached to the printed circuit board assembly 908. The digital processor 902 is programmed to be responsive to monitored testing gas parameter readings obtained by the gas sensor assembly 22 that are performed over one or more time intervals for monitoring performance of the gas monitor apparatus 12. As noted, in this embodiment, the digital processor 902 is implemented as a microcontroller, such as is available from Microchip Technology Inc. of Chandler, Ariz., USA. The digital processor 902 may also be implemented in hardware, such as an Application Specific Integrate Circuit (ASIC) on a semiconductor chip. The digital processor 902 is preprogrammed with suitable applications to perform the normal mode operations mentioned above, but also the testing mode operation of this invention that are described below.

The digital processor 902 sends and receives instructions and data to and from each of the system components that are coupled to the interconnect bus 904 to perform system operations based on the requirements of firmware applications that include a firmware application 924 for normal mode operation of the gas monitor apparatus and a testing mode module firmware application 926. In the normal mode of operation, the gas sensor is operable for responding in its typical time frame to gas, which as noted can be considerable. These firmware applications 924 and 926 may be stored in a permanent or non-volatile memory device, such as flash memory 932, or some other suitable non-volatile memory device(s) that would be appropriate for the data being handled. The program code of the firmware applications 924 and 926 are executed from the flash memory 932 under control of the digital processor 902. The random access memory (RAM) 930 is used to store the data during firmware execution. While the testing mode application 926 is implemented as firmware executable by the processing unit, it may be implemented as hardware (e.g. circuitry). The testing mode application operates the digital processor 902 to activate the display 922 for indicating pass/fail conditions. An electrically erasable programmable read only memory (EEPROM) 928 may also be used and contains other data, such as the predefined parameter values associated with the operating characteristics of the gas sensor assembly 22 as described below.

Figure 8:
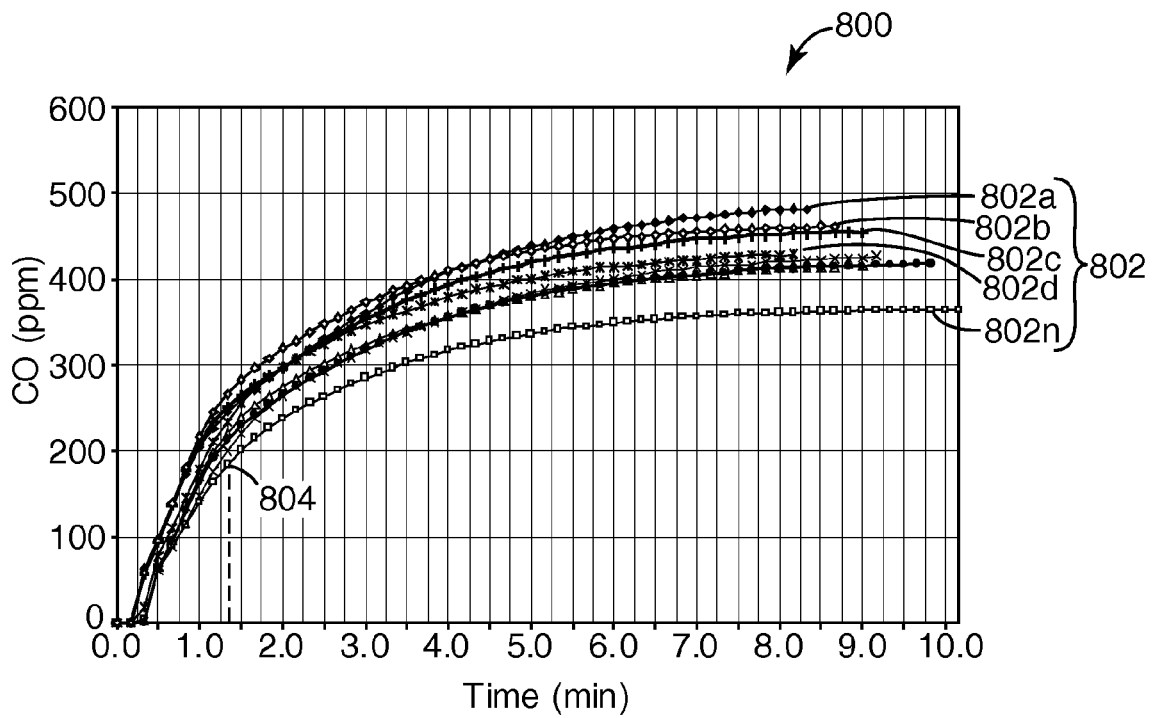
FIG. 8 is a graph illustrating response curves of gas sensor assemblies that may be utilized in the gas monitor apparatus depicted in FIGS. 2 and 3

FIG. 8 illustrates a sensor response graph 800 of a series of individual curves $802_{a-n}$ (collectively 802) plotted from a series of previous sample tests generated by gas sensors of the type that fall within a group or class of sensors to which the present gas sensor assembly 22 is similar (e.g., semiconductor sensors) and which have been validated. In this embodiment, the predefined parameter values with which the response of the gas sensor assembly 22 is to be validated against are the values associated with a selected one of the gas sensor response curves 802, as will be explained. According to this invention, it was determined that the curve 802 with the lowest slope (e.g. $802_n$) as viewed in the gas sensor response graph 800 is one that is considered to represent the slowest response time of an otherwise acceptable operating gas sensor that has been validated. In taking into account the different response characteristics of gas monitors, the present invention selected typical responses of a gas sensor after significant exposure to CO. The response curves generated after long gas exposure are considered to have the lowest response time. As such, the slowest acceptable response curve may be selected for purposes of comparing to the gas sensor assembly 22 for validation purposes. Alternatively, a sensor response graph may be generated based on previous validation responses of the actual gas sensor assembly 22 instead of being compared to a group of similar sensors.

In this alternative example, the response curve that is the lowest (lowest slope), as viewed in a response graph (FIG. 8) may be selected to yield a response curve that has the slowest response that would otherwise validate the response of the gas sensor assembly 22. It will be appreciated that the slowest or less responsive curve is used for defining one limit or boundary of acceptable gas monitor performance. As will be described below other response curves (e.g., the fastest or most responsive) may be used and which define another limit or boundary of acceptable gas monitor performance according to this invention.

The graphs generated are exemplary of many that may be used. It may further be appreciated that a sensor may not have the same response to a particular gas if some environmental conditions change. There are many uncontrolled variables that affect sensor responses. For example, variables like humidity, temperature, and a natural spread of readings in a group of monitors also affect a response curve. Thus, it will be appreciated that the curves presented herein can change based on such a wide number of variables. Nevertheless, according to the present invention, at least one of a series of generated curves can be selected and used for comparison purposes in the manner described below. In an illustrated embodiment, the curve selected may reflect the slowest acceptable response. As will be explained below, other sensor response curves to CO could be obtained, such as a typical first exposure to gas response (fastest or most responsive type of curve). Responses at different levels of testing gas concentration (e.g., 100 ppm, etc.) can also be utilized.

As noted, the curve $802_n$ is considered to represent a response that is close to the slowest response of a properly functioning gas sensor. This is considered satisfactory for validating the gas sensor assembly 22. The slope or rate-of-rise of the curve sensor response curve $802_n$ indicates a rate-of-rise of values or slope that will lead to an equilibrium response or equilibrating state of the gas sensor assembly within a predetermined time interval considered validating by, for example, a manufacturer. As noted, "equilibrium response" used in the specification and claims defines a response, such that gas reading values of the gas sensor assembly 22 of the gas monitor apparatus 12 being tested no longer increases. According to this embodiment, the curve $802_n$ has been used to define a predetermined rate-of-rise value used for comparison purposes for validation. As such it will set one of the two bounds of acceptable gas monitor performance. The predetermined rate-of-rise value is obtained after a predetermined time has elapsed (e.g., one (1) minute) following the gas sensor value obtaining a reading or threshold value of 30 ppm (the threshold value is the validating rating of the gas sensor assembly 22 being tested). The point 804 on the response curve $802_n$ indicates a sensor reading after the predetermined time (i.e., 1 min.) has elapsed following the threshold value being reached. As an example, the value at point 804 is a reading of 170 ppm. The predetermined rate-of-rise value is computed by taking the value of 170 ppm and subtracting 30 ppm (validating or threshold value of the gas sensor). After such computation, the difference measures 140 ppm. Since the predetermined time interval is one (1) minute, the rate-of-rise is 140 ppm/minute. Other suitable time intervals can be utilized for determining the slope.

To provide a safety factor in order to be conservative, the value of 140 ppm/minute was multiplied by a safety factor of 50%. Although the safety factor value of 50% is selected for this gas monitor, the safety factor value may be different for other devices and/or as more data becomes available. The approach taken in this embodiment is to establish bounds for an acceptable response of a gas sensor to pass the test. Acceptable safety factor values might be in a range of greater or lesser than 50% according to this invention. Safety factor values utilized for defining the bounds of the slowest response curve take into account known variables that affect response times of sensors. In this manner, the predetermined rate-of-rise value will not cause a failure reading when in fact none exist. It will be appreciated that a wide range of acceptable safety factor values might be utilized and these examples should not be considered limiting.

Referring back to FIG. 8, if the gas sensor assembly is later tested and has a rate-of-rise value at least reaching at least 70 ppm/minute, such will indicate that the gas sensor assembly has "passed" the test and is considered operable in the intended manner. Alternatively, if a test rate-of-rise value is less than 70 ppm/minute, then the gas sensor assembly will "fail" the test and be considered inoperable for the purposes intended. While, the exemplary value of 70 ppm/minute is selected other suitable values can be selected. For example, the rate-of-rise value can fall within a band or range determined to be accepted for residential and commercial use.

Other factors may cause the gas sensor assembly 22 to alarm prematurely. Sensors typically fail manufacturer or industry standards if they react too slowly, or too fast. For example, a gas sensor assembly may respond prematurely fast (outside the bounds of acceptable performance) if a resistor (not shown) of the electronic control assembly malfunctions. Therefore, the present invention contemplates having a second predetermined rate-of-rise value that can be compared against to see if the gas monitor apparatus properly functions. This will be explained below. In this regard, reference is made to FIGS. 11 and 12 for illustrating how a second predetermined rate-of-rise value is generated.

The monitoring application defines a gas testing process 1000 that will validate the gas sensor assembly 22 being validated. Essentially, the monitoring application, awaits initiation of the testing mode. This is achieved after the actuator switch is activated by a user. In this embodiment, the actuator switch 914 is rapidly and sequentially activated within several seconds by the user to invoke or commence the testing mode by the testing mode module 926. Such a signal differentiates its function relative to other functions that may be initiated by the switch.

Figure 10:
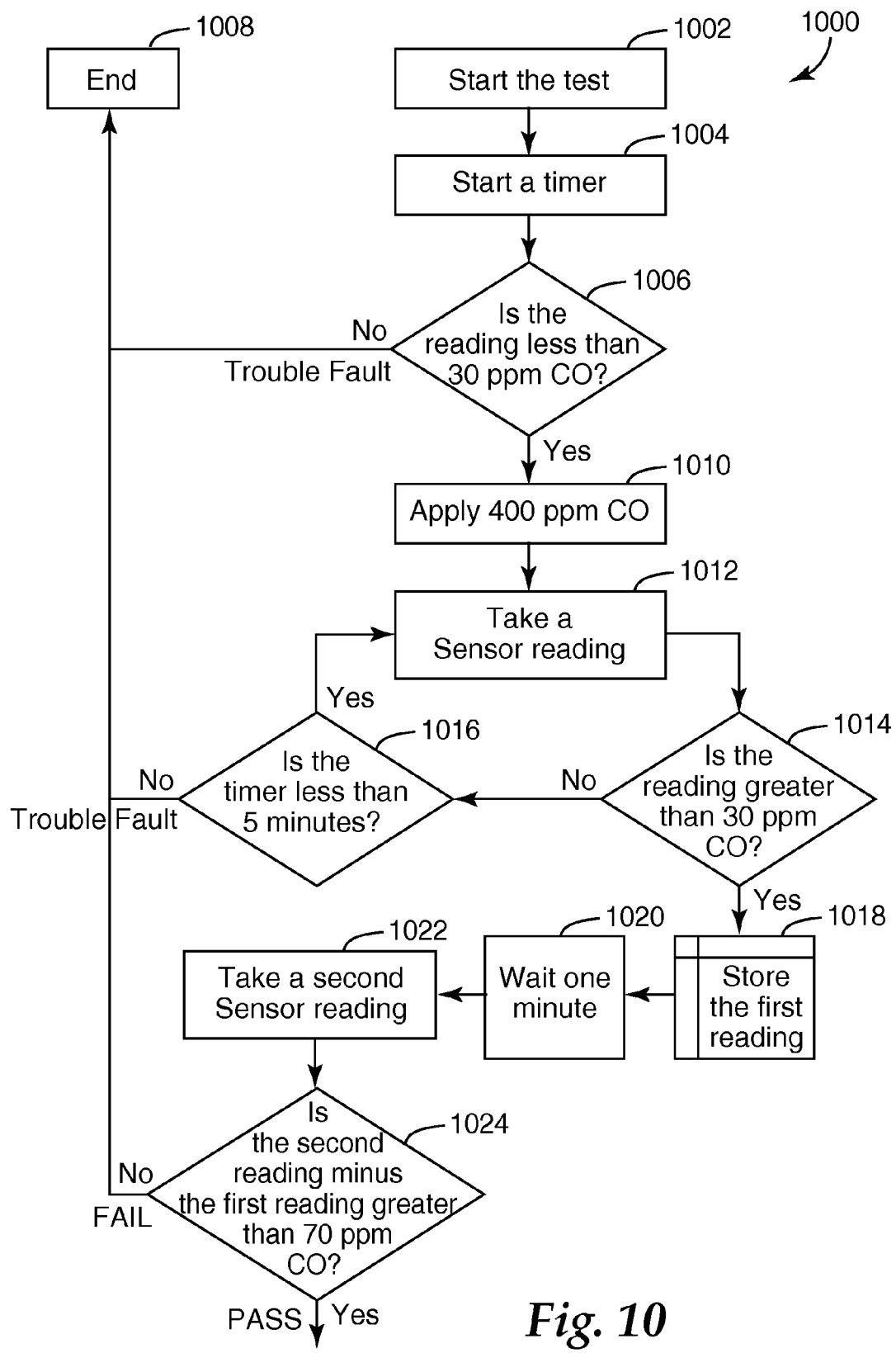
FIG. 10 is a flow diagram illustrating one aspect of an improved testing process of this invention wherein a digital processor is mounted within the gas monitor.

Reference is now made to FIG. 10 for illustrating one embodiment of a gas testing process 1000 implemented by using the gas monitor apparatus testing mode application 926 according to the present invention. In block 1002, the gas testing process 1000 commences. A test administrator or inspector will attach the fluid coupling apparatus 16, with the tubing 24 attached to the regulator 20, to the electronic control assembly 900 as described above wherein the gas delivery opening is aligned with the gas sensor assembly. As a result, the testing gas can be sensed by the gas sensor assembly 22 when actually applied as will be explained below. The testing gas utilized has a concentration selected to trigger the alarm. For example, the testing gas has a concentration of 400 ppm which not only exceeds the concentration response of the gas monitor apparatus 12 (e.g., 30 ppm) utilized but also insures a quicker testing process. Other concentrations of testing gas may be utilized to test the monitor. Generally, the lower the concentration of gas utilized for testing the longer the test of this invention.

According to this embodiment, it is desired that prior to running the testing process 1000, the air surrounding the gas monitor apparatus 12 should be clear of concentrations of carbon monoxide that exceed the minimum concentration response (e.g., 30 ppm) of the gas monitor apparatus 12. Towards this end, the testing process 1000 proceeds to start timer block 1004 whereby the gas sensor assembly 22 obtains a first reading. Following obtaining the first reading, the testing process 1000 proceeds to a decision block 1006, whereat a preliminary determination is made as to whether or not the air surrounding the gas monitor apparatus is clear of concentrations higher than the minimum concentration value (e.g., 30 ppm) of the gas monitor apparatus in order for the testing process 1000 to pass.

At block 1006, a determination is made as to whether the reading is less than 30 ppm. If the determination is negative (i.e., No) a troubled fault is reached, If the reading value does at least reach the minimum concentration response of 30 ppm, that is indicative that the air surrounding the monitor is unclear. Hence, a troubled fault is recognized at a fault block 1008 which thereby ends the testing process. As such, the tester or user will try to clear the air surrounding the gas monitor. Alternatively, if the decision in the decision block 1006 is affirmative (i.e. Yes) then the testing process 1000 proceeds to the apply gas block 1010, whereat the tester or user opens the regulator 20 to allow carbon monoxide to travel to the fluid coupler body 70.

Following the application of the testing gas, the testing module obtains another reading which is taken by the gas sensor assembly 22 at the take sensor reading block 1012. At decision block 1014, a determination is made as to whether or not this previous reading at least reaches a threshold value that is related to the response of the gas sensor assembly. In the illustrated embodiment, 30 ppm is considered the threshold value which is the minimum concentration response of the gas monitor apparatus 12. If the determination in the decision block 1014 is negative (i.e., No), the testing process 1000 then proceeds to the decision block 1016 whereat a decision is made if the timer has been running for less than five (5) minutes. In particular, at the decision block 1016, if a determination is made that the timer has been running for less than five (5) minutes then the testing process 1000 loops back to take a subsequent sensor reading block 1012. Other reasonable times are contemplated besides five (5) minutes. The testing process 1000 will continue this loop until either the decision in the block is indicative of a reading that the gas sensor assembly has read a value that at least reaches 30 ppm or the timer has exceeded five (5) minutes of running time and the read value has not at least reached 30 ppm. In the latter case, the testing process 1000 proceeds to the fault block 1008 to indicate that the gas reading is indicative of the fault condition whereby the testing process 1000 terminates.

If the decision of the decision block 1014 is affirmative (i.e., Yes) then the testing process 1000 stores this first reading in the reading store block 1018 in the RAM memory. Thereafter, the testing process 1000 introduces a time delay of a predetermined time by a time delay block 1020 for enabling the taking of a second reading by the gas sensor assembly in the second reading block 1022. In the illustrated embodiment the time delay introduced by the time delay block 1020 is one minute. Of course, other time delays may be utilized depending on the nature of the gas being tested.

Following the second reading, after the predetermined time interval, the testing process 1000 then proceeds to the decision block 1024. In the decision block 1024, testing module application 926 of this invention is utilized to predict if the minimum concentration response of the gas sensor assembly after 1 minute at least reaches a predetermined rate-of rise parameter value (e.g. 70 ppm/minute). Hence, the testing module application 926 determines if the monitor is operative or not within a short period of time without having to the test for a typical testing period.

If the determination is affirmative (YES), then a passing condition (i.e., "passes") of the gas monitor apparatus 12 is achieved by the testing process 1000. Alternatively, if the testing module application 926 determines that the gas monitor apparatus 12 does not at least reach the 70 ppm/minute then the testing process 1000 proceeds to the fault block 1008, whereby the testing process ends. This is indicative of the gas monitor apparatus 12 not passing the test of this invention.

Figure 11:
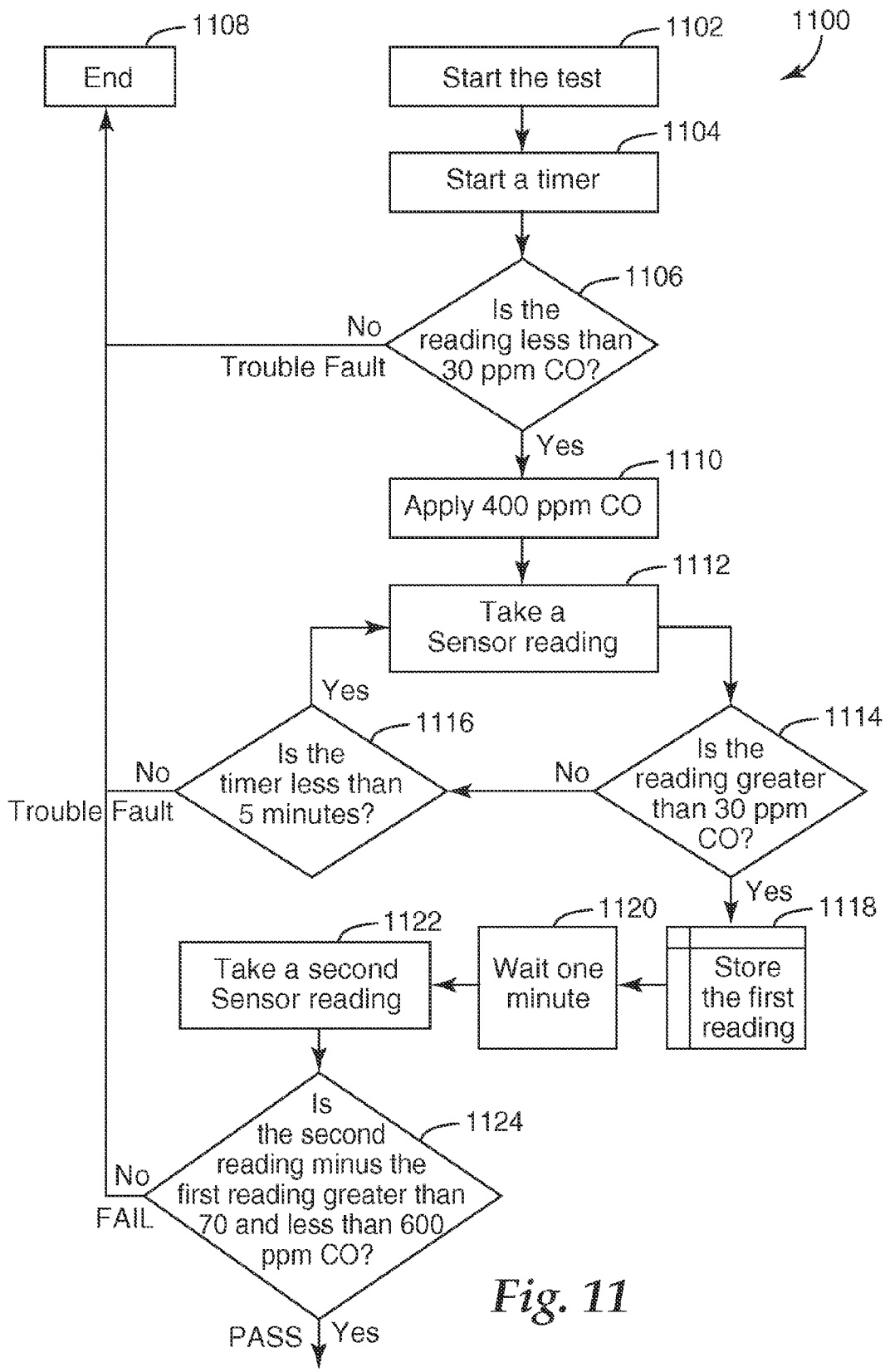
FIG. 11 is a flow diagram illustrating another aspect of an improved testing process of this invention.
Figure 12:
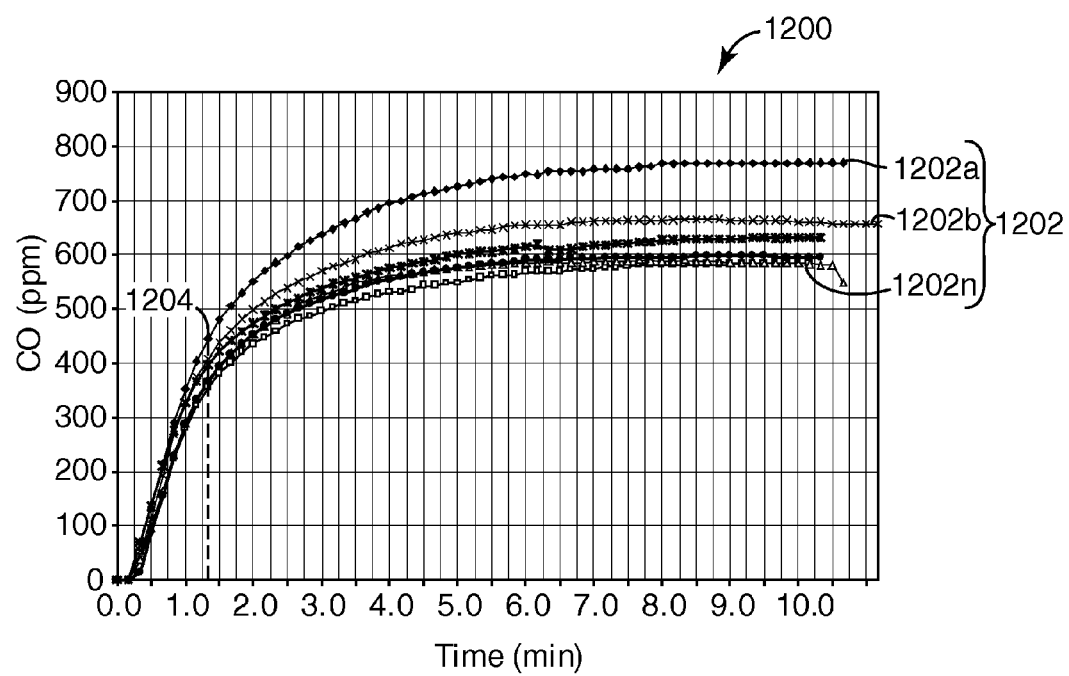
FIG. 12 is a graph illustrating response curves of gas sensor assemblies that may be utilized in this invention.

Reference is made to FIGS. 11 & 12, for describing an alternate embodiment of the present invention. Initial reference is made to FIG. 12 illustrates a sensor response graph 1200 of a series of individual curves $1202_{a-n}$ (collectively 1202) plotted from a series of previous sample tests generated by gas sensors of the type that fall within a group or class of sensors to which the present gas sensor assembly 22 is similar (e.g., semiconductor sensors) and which have been validated. In this embodiment, the predefined parameter values with which the response of the gas sensor assembly 22 is to be validated against are the values associated with a selected one of the gas sensor response curves 1202, as will be explained. According to this invention, it was determined that the curve 1202 with the highest slope (e.g. $1202_a$), as viewed in the gas sensor response graph 1200, is one that is considered to represent the fastest response time of an otherwise acceptable operating gas sensor that has been validated. In taking into account the different response characteristics of gas monitors, the present embodiment selected typical responses of a gas sensor that have not been exposed to CO for a considerable period of time. Unlike the response curves noted above that were generated after long gas exposure, these are generated following first exposure of a sensor to the gas. As used in the present application "first exposure" is considered to be the first exposure of the sensor to gas after a prolonged time that the sensor has not sensed gas. The prolonged time period may be as short as four (4) weeks or even longer. As such, the fastest acceptable response curve may be selected from one of these response curves for purposes of comparing it to the response of the gas sensor assembly 22 for validation purposes of the upper limit to an acceptable range of performance. Alternatively, a sensor response graph may be generated based on previous validation responses of the actual gas sensor assembly 22 instead of being compared to a group of similar sensors.

As noted, the curve $1202_a$ is considered to represent a response that is close to the fastest response of a properly functioning gas sensor. This is considered satisfactory for validating the gas sensor assembly 22. According to this embodiment, the curve $1202_a$ has been used to define a predetermined rate-of-rise value used for comparison purposes for validation. As such it will set one of the two bounds of acceptable gas monitor performance. The predetermined rate-of-rise value is obtained after a predetermined time has elapsed (e.g., one (1) minute) following the gas sensor value obtaining a reading or threshold value of 30 ppm (the threshold value is the validating rating of the gas sensor assembly 22 being tested). The point 1204 on the response curve $1202_a$ indicates a sensor reading after the predetermined time (i.e., 1 min.) has elapsed following the threshold value being reached. As an example, the value at point 1204 is a reading of about 427 ppm. This is the value of a reading 60 seconds later than a 30 ppm reading (validating or threshold value of the gas sensor assembly). The predetermined rate-of-rise value is computed by taking the value of 427 ppm and subtracting 30 ppm (validating or threshold value of the gas sensor assembly 22). After such computation, the difference measures 397 ppm. Since the predetermined time interval is one (1) minute, the rate-of-rise is 397 ppm/minute. Other suitable time intervals can be utilized for determining the slope.

If we use a 150% safety factor, the maximum rate of rise is (427−30)*1.5=596 ppm/min. This has been approximated to 600 ppm/minute. Acceptable safety factor values might be in a range of greater or lesser than 150% according to this invention. Safety factor values utilized for defining the bounds of the fastest response curve take into account known variables that affect response times of sensors. In this manner, the predetermined rate-of-rise value will not cause a failure reading when in fact none exist. It will be appreciated that a wide range of acceptable safety factor values might be utilized and these examples should not be considered limiting.

FIG. 11 represents another testing process 1100 according to this invention. This embodiment presents an embodiment wherein first and second predetermined rate-of-rise values are utilized to define bounds or a range of acceptable validating performances of the gas monitor apparatus 12. The testing process 1100 is similar to the testing process 1000 described above. In particular, the blocks 1102-1122 perform substantially the same processes as those described above in corresponding blocks 1002-1022. Hence, a discussion of the functions of the blocks 1102-1122 is not presented herein. A difference between the testing process 1100 and the testing process 1000 is that in block 1124, first and second predetermined rates-of-rises are used to define lower and upper bounds or range of acceptable validating performance. Thus, the testing module application 924 includes the functions of the block 1124 which will be described below in the context of FIG. 12. In the decision block 1124, testing module application 926 of this invention is utilized to predict if the minimum concentration response of the gas sensor assembly after 1 minute at least reaches a first predetermined rate-of rise parameter value (e.g. 70 ppm/minute) for one limit or bound (e.g., slowest response considered acceptable) and if it does not exceed a second predetermined rate-of-rise value of 600 ppm/minute for another limit or bound (e.g., fastest response considered acceptable) of an acceptable range of performance. Hence, the testing module application 926 determines if the monitor is operative or not within a short period of time without having to test for a typical testing period. For instance, with 400 ppm, testing may be accomplished either in about or less than 1½ minutes. This approach represents a significant reduction in testing time compared to known approaches using, for example, equilibrium responses. If an equilibrium test were conducted, as noted above, on a gas sensor being used in the present illustrated embodiment, the sensor could be validated in about 4.5 to about 5 minutes (or about at least 300% more time). Hence, the testing of this invention reduces significantly the testing time.

As such if the determination is affirmative (YES) in the block 1124 then the gas monitor apparatus 12 "passes" the testing process 1100. Stated differently, for a passing condition to exist, the rate-of-rise value during the test must at least reach 70 ppm/minute and must not exceed 600 ppm/minute. Alternatively, if the testing module application 926 determines that the gas monitor apparatus 12 does exceed 600 ppm/minute then the testing process 1100 proceeds to the fault block 1108, whereby the testing process 1100 ends. This is indicative of the gas monitor apparatus 12 not passing or failing the test of this invention because its response is either too fast or slow based on a comparison with the bounds of acceptable gas monitor performance.

The above embodiments have been described as being accomplished in a particular sequence, it will be appreciated that such sequences of the operations may change and still remain within the scope of the invention. For example, an illustrated embodiment discusses one set of testing protocols wherein the minimum validation value for the gas monitor must be satisfied before apply testing gas to obtain a first reading. It will be appreciated that such preliminary procedures need not be followed for one to conduct testing of gas sensor assemblies. Also, other procedures may be added.

This invention may take on various modifications and alterations without departing from the spirit and scope. Accordingly, this invention is not limited to the above-described embodiments, but is to be controlled by limitations set forth in the following claims and any equivalents thereof.

This invention also may be suitably practiced in the absence of any element not specifically disclosed herein. All patents and publications noted above, including any in the Background section are incorporated by reference into this document in total.

What is claimed is:

1. A method of testing performance of a gas sensor assembly capable of monitoring a toxic gas, comprising:
   providing a gas sensor assembly capable of monitoring a toxic gas;
   providing a fluid coupling apparatus;
   applying a testing gas adjacent the gas sensor assembly from the fluid coupling apparatus;
   obtaining a first reading value of testing gas;
   storing the first reading value;
   obtaining a second gas sensor assembly reading value;
   determining a rate-of-rise value of the first and second reading values of the gas sensor based on a difference of the first and second reading values relative to a testing time interval therebetween; and
   determining if a gas sensor assembly passing condition exists based on a comparison of the rate-of-rise value of the first and second reading values to at least a first predefined rate-of-rise value of the gas sensor assembly;
   wherein the passing condition exists if the rate-of-rise value of the first and second reading values at least reaches the first predefined rate-of-rise value and if the rate-of-rise value of the first and second reading values does not exceed a second predefined rate-of-rise value.

2. The method of claim 1, wherein the first predefined rate-of-rise value if at least reached is indicative of a passing condition that validate operation of the gas sensor assembly.

3. The method of claim 1, wherein the testing time interval is about 1 minute.

4. The method of claim 1, wherein the second predefined rate-of-rise value if exceeded is indicative of a condition that the gas sensor assembly is not being validated.

5. The method of claim 1, wherein the testing gas concentration is applied at a specific concentration value associated to the gas sensor assembly.

6. The method of claim 5, wherein the specific concentration of testing gas would trigger a gas monitor alarm.

7. The method of claim 1, wherein the first and second predetermined rate-of-rise values define bounds of acceptable validating performance of the gas sensor assembly.

8. The method of claim 1, wherein the testing gas comprises carbon monoxide.

9. The method of claim 1, wherein the toxic gas comprises carbon monoxide.

10. A method of testing performance of a gas sensor assembly capable of monitoring a toxic gas, comprising:
    providing a gas sensor assembly capable of monitoring a toxic gas;
    providing a fluid coupling apparatus;
    determining if a testing threshold value is obtained before applying the testing gas to obtain the first reading value, which testing threshold value is a minimum value for which the gas sensor assembly is validated;
    applying a testing gas adjacent the gas sensor assembly from the fluid coupling apparatus;
    obtaining a first reading value of testing gas;
    storing the first reading value;
    obtaining a second gas sensor assembly reading value;
    determining a rate-of-rise value of the first and second reading values of the gas sensor based on a difference of the first and second reading values relative to a testing time interval therebetween; and
    determining if a gas sensor assembly passing condition exists based on a comparison of the rate-of-rise value of the first and second reading values to at least a first predefined rate-of-rise value of the gas sensor assembly.

11. The method of claim 10, wherein the testing gas comprises carbon monoxide.

12. The method of claim 10, wherein the testing time interval between obtaining the first and second reading values is no more than about 1 min.

13. The method of claim 10, wherein the testing gas concentration is applied at a specific concentration value that would trigger a gas monitor alarm.

14. A method of testing performance of a gas monitor apparatus, comprising:
    providing a field test kit assembly;
    applying a testing gas adjacent a gas monitor apparatus from the field test kit assembly;
    obtaining a first reading value of testing gas;
    storing the first reading value;
    obtaining a second reading value of testing gas;
    determining a rate-of-rise value of the first and second reading values based on a difference of the first and second reading values relative to a testing time interval therebetween; and
    determining if a gas monitor apparatus passing condition exists based on a comparison of the rate-of-rise value of the first and second reading values to at least a first predefined rate-of-rise value of a gas monitor apparatus;
    wherein the passing condition exists if the rate-of-rise value of the first and second reading values at least reaches the first predefined rate-of-rise value and if the rate-of-rise value of the first and second reading values does not exceed a second predefined rate-of-rise value.

15. The method of claim 14, wherein the first and the second predetermined rate-of-rise values define bounds of acceptable validating performance of a gas monitor apparatus.

16. The method of claim 14, wherein each of the first and the second predetermined rate-of-rise values include a safety factor.

17. The method of claim 14, wherein the testing time interval between obtaining the first and second reading values is no more than about 1 min.

18. The method of claim 14, wherein the testing gas comprises carbon monoxide.

19. The method of claim 14, wherein the testing gas concentration is applied at a specific concentration value that would trigger a gas monitor alarm.

* * * * *